United States Patent
Sharma et al.

(10) Patent No.: US 8,481,595 B2
(45) Date of Patent: Jul. 9, 2013

(54) COMPOUNDS FOR THE TREATMENT OF METABOLIC DISORDERS

(75) Inventors: Shalini Sharma, Gaithersburg, MD (US); Reid W. von Borstel, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 266 days.

(21) Appl. No.: 12/812,514

(22) PCT Filed: Jan. 13, 2009

(86) PCT No.: PCT/US2009/030845
§ 371 (c)(1),
(2), (4) Date: Jul. 12, 2010

(87) PCT Pub. No.: WO2009/091732
PCT Pub. Date: Jul. 23, 2009

(65) Prior Publication Data
US 2010/0286267 A1    Nov. 11, 2010

Related U.S. Application Data

(60) Provisional application No. 61/021,061, filed on Jan. 15, 2008, provisional application No. 61/096,576, filed on Sep. 12, 2008.

(51) Int. Cl.
*A01N 37/10*    (2006.01)
*A61K 31/325*   (2006.01)
*C07C 69/76*    (2006.01)

(52) U.S. Cl.
USPC .......................................... 514/533; 560/109

(58) Field of Classification Search
USPC .......................................... 514/533; 560/109
See application file for complete search history.

(56) References Cited

U.S. PATENT DOCUMENTS

| | | | |
|---|---|---|---|
| 3,772,389 A | 11/1973 | Lawrance et al. | |
| 4,948,809 A | 8/1990 | Witte et al. | |
| 6,677,473 B1 | 1/2004 | Madison et al. | |
| 6,858,602 B2 | 2/2005 | Sharma et al. | |
| 6,916,848 B2 | 7/2005 | Sharma | |
| 6,924,314 B2 | 8/2005 | Sharma et al. | |
| 6,946,491 B2 | 9/2005 | Sharma et al. | |
| 7,012,071 B2 | 3/2006 | Sharma et al. | |
| 7,041,659 B2 | 5/2006 | Sharma | |
| 7,045,541 B2 | 5/2006 | Sharma | |
| 7,101,910 B2 | 9/2006 | Sharma | |
| 7,192,982 B2 | 3/2007 | Brooks et al. | |
| 7,329,782 B2 | 2/2008 | Sharma et al. | |
| 7,361,686 B2 | 4/2008 | Hodge et al. | |
| 7,442,796 B2 | 10/2008 | Sharma et al. | |
| 7,514,555 B2 | 4/2009 | Hodge et al. | |
| 7,547,802 B2 | 6/2009 | Sharma | |
| 7,605,181 B2 | 10/2009 | Hodge et al. | |
| 7,615,575 B2 | 11/2009 | Hodge et al. | |
| 7,645,772 B2 | 1/2010 | Hodge et al. | |
| 7,749,990 B2 | 7/2010 | Hodge et al. | |
| 7,820,721 B2 | 10/2010 | Sharma et al. | |
| 7,851,494 B2 | 12/2010 | Sharma et al. | |
| 7,863,475 B2 | 1/2011 | Sharma | |
| 7,906,675 B2 | 3/2011 | Sharma | |
| 7,915,429 B2 | 3/2011 | Sharma et al. | |
| 7,932,290 B2 | 4/2011 | Sharma et al. | |

(Continued)

FOREIGN PATENT DOCUMENTS

| | | | |
|---|---|---|---|
| DE | 949521 | * | 9/1956 |
| JP | 4-139151 | | 5/1992 |
| JP | 08048664 | * | 2/1996 |

OTHER PUBLICATIONS

Singh et al. (Indian J of Chemistry, 2006, 1554-1557).*
Pending claims (as of Feb. 24, 2011) of U.S. Appl. No. 13/034,201.
Marfak, et al., "Radiolysis of Kaempferol in Water/Methanol Mixtures. Evaluation of Antioxidant Activity of Kaempferol and Products Formed", J. Agric. Food Chem., 51(5): 1270-1277; 2003.
Irie, et al., Use of Potassium Peroxodisulfate for Benzylic Oxidation and Oxidative Coupling of Benzoylacetates, Synlett, 7:421-423, Jul. 1990.

(Continued)

*Primary Examiner* — Sreeni Padmanabhan
*Assistant Examiner* — Uma Ramachandran
(74) *Attorney, Agent, or Firm* — Lewis J. Kreisler

(57) ABSTRACT

Agents useful for the treatment of various metabolic disorders, such as insulin resistance syndrome, diabetes, polycystic ovary syndrome, hyperlipidemia, fatty liver disease, cachexia, obesity, atherosclerosis and arteriosclerosis are disclosed. The agent is a compound of Formula (I): wherein m is 0, 1, 2, 3, 4, 5, 6, 7 or 8; $R^1$ is hydrogen or alkyl having from 1 to 3 carbon atoms; and $R^2$ is hydrogen, halo, alkyl having from 1 to 3 carbon atoms, or alkoxy having from 1 to 3 carbon atoms. A is phenyl, unsubstituted or substituted by 1 or 2 groups selected from: halo, hydroxy, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; Alternatively, the agent can be a pharmaceutically acceptable salt of the compound of Formula (I).

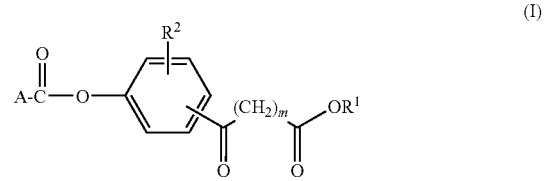

(I)

12 Claims, No Drawings

U.S. PATENT DOCUMENTS

| | | |
|---|---|---|
| 7,935,689 B2 | 5/2011 | Sharma et al. |
| 7,947,735 B2 | 5/2011 | Sharma et al. |
| 7,973,052 B2 | 7/2011 | Hodge et al. |
| 2005/0090555 A1 | 4/2005 | Sharma et al. |
| 2006/0035970 A1 | 2/2006 | Hodge et al. |
| 2007/0105958 A1 | 5/2007 | Sharma et al. |
| 2007/0244172 A1 | 10/2007 | Sharma et al. |
| 2009/0176889 A1 | 7/2009 | Sharma et al. |
| 2009/0203793 A1 | 8/2009 | Romantsev et al. |
| 2010/0227809 A1 | 9/2010 | Wolpe et al. |
| 2010/0227901 A1 | 9/2010 | Sharma et al. |
| 2010/0234464 A1 | 9/2010 | Sharma et al. |
| 2010/0292277 A1 | 11/2010 | von Borstel et al. |

OTHER PUBLICATIONS

Patani, et al. "Biososterism: A Rational Approach in Drug Design", Chemical Reviews, 96(8):3152-3154, 1996.

Abstract of Japanese Patent No. 4-139151 published May 13, 1992.

* cited by examiner

COMPOUNDS FOR THE TREATMENT OF METABOLIC DISORDERS

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

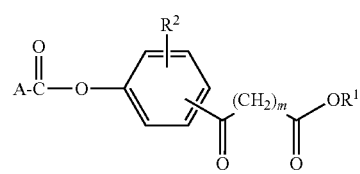

wherein m is 0, 1, 2, 3, 4, 5, 6, 7 or 8; $R^1$ is hydrogen or alkyl having from 1 to 3 carbon atoms; $R^2$ is hydrogen, halo, alkyl having from 1 to 3 carbon atoms, or alkoxy having from 1 to 3 carbon atoms; and A is phenyl, unsubstituted or substituted by 1 or 2 groups selected from: halo, hydroxy, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon. Alternatively, the biologically active agent can be a pharmaceutically acceptable salt of the compound of Formula I.

This invention is based on the finding that 4-(3-(2,6-Dimethylbenzoyloxy)phenyl)-4-oxobutanoic acid, a biologically active agent of this invention, showed activity in the biological activity assay described below, which is an established animal models of human diabetes and insulin resistance syndrome.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. The corresponding structure appears below its name. Compound DP is included within the scope of Formula I shown above.

DP 4-(3-(2,6-Dimethylbenzoyloxy)phenyl)-4-oxobutanoic acid

As used herein the transitional term "comprising" is open-ended. A claim utilizing this term can contain elements in addition to those recited in such claim.

Compounds of the Invention

In an embodiment of the agent, use, method or pharmaceutical composition described in the Summary above, m is 2 or 4. In an embodiment of this invention $R^2$ is hydrogen. In an embodiment of this invention A is phenyl, unsubstituted or substituted by 1 or 2 groups selected from: halo, hydroxy, alkyl having 1 or 2 carbon atoms, perfluoromethyl, alkoxy having 1 or 2 carbon atoms, and perfluoromethoxy. In a more specific embodiment A is 2,6-disubstituted phenyl, with the substituents as described above. Protection against cleavage by esterases is conferred when the substituents at the 2- and 6-positions are independently selected from the group consisting of: chloro, bromo, iodo, hydroxy, alkyl having 1 or 2 carbon atoms, perfluoromethyl, alkoxy having 1 or 2 carbon atoms, and perfluoromethoxy. For high activity and protection against cleavage by esterases, chloro, bromo, iodo, hydroxy, alkyl having 1 or 2 carbon atoms, and perfluoromethyl substitutions at the 2- and 6-positions are preferred. In a still more specific embodiment A is 2,6-dimethylphenyl. In a specific embodiment of this invention the compound is 4-(3-(2,6-Dimethylbenzoyloxy)phenyl)-4-oxobutanoic acid.

In an embodiment of the biologically active agent of this invention, the agent is in substantially (at least 98%) pure form.

Reaction Schemes

The compound of formula I where m is 0, $R^2$ is hydrogen, halo, alkoxy having from 1 to 3 carbon atoms or alkyl having from 1 to 3 carbon atoms, and $R^1$ is hydrogen or alkyl having from 1 to 3 carbon atoms, i.e. compounds of formula:

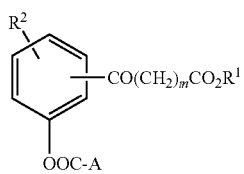

(I)

wherein A is described as above, can be prepared via reaction of Scheme 1.

In the reaction scheme of Scheme 1, A, $R^1$ and $R^2$ are as above. Y is chloro or bromo group, preferred group being chloro.

The compound of formula II is converted to the compound of formula V via reaction of step (a) using condensation of II with III using coupling reagent for example 1-(3-dimethylaminopropyl)-3-ethylcarbodiimide hydrochloride in the presence of catalytic amount of 4-di(methylamino)pyridine. The other dehydrating reagent includes but is not limited to dicyclohexylcarbodiimide. The reaction is carried out in a suitable solvent for example dichloromethane, N,N-dimethylformamide and the like. Any of the conditions conventionally used in such coupling reactions can be utilized to carry out the reaction of step (a).

The compound of formula V can also be prepared by acylation of the compound of formula II with the compound of formula IV via the reaction of step (b) by using suitable base for example sodium hydride, triethylamine, pyridine and the like. Any conventional conditions to acylate a hydroxyl group with a halo group can be utilized to carry out the reaction of step (b). The reaction of step (b) is preferred over step (a) if the compound of formula IV is readily available.

The compound of formula V is converted to the compound of formula VII via reaction of step (c) by oxidation of methyl group with selenium dioxide (VI) in the presence of pyridine. Generally the reaction is carried out at temperatures of from 25° C.-100° C. Any of the conditions conventionally used in such oxidation reactions can be utilized to carry out the reaction of step (c).

The compound of formula VII is the compound of formula I where m is 0 and $R^1$ is H.

The compound of formula VII can be converted to the compound of formula I where $R^1$ is alkyl having from 1 to 3 carbon atoms by esterification using $C_1$-$C_3$ alkyl chloroformate in the presence of base for example triethylamine, pyridine and the like, or by using dehydrating reagents for example 1-(3-dimethylaminopropyl)-3-ethylcarbodiimide hydrochloride in the presence of catalytic amount of 4-di(methylamino)pyridine or using dehydrating reagent for example dicyclohexylcarbodiimide or by direct reaction with the compound of formula VII with $C_1$-$C_3$ alkyl alcohol in the presence of catalytic amount of acid for example $H_2SO_4$, TsOH and the like. Generally the reaction is carried out in solvents such as ethyl acetate, dichloromethane, tetrahydrofuran, N,N-dimethylformamide and the like. Generally the reaction is carried out at temperatures of from 0° C. to 25° C. Any of the conditions conventionally used in such esterification reactions can be utilized to carry out the reaction of step (d).

If A is phenyl substituted by 1 or 2 groups of hydroxyl, it is generally preferred to protect the hydroxyl group with the suitable protecting group which protects the hydroxyl groups throughout the reaction. The suitable protecting group can be described in the Protective Groups in Organic Synthesis by T. Greene. The protecting group can be removed after the oxidation in the case of compound of formula I where $R^1$ is H but for the compound of formula where $R^1$ is alkyl having from 1 to 3 carbon atoms, deprotection can be performed utilizing suitable deprotecting reagents such as those described in Protective Groups in Organic Synthesis by T. Greene after the reaction of step (d).

The products from each step can be isolated and purified by techniques such as extraction, evaporation, chromatography, and recrystallization.

Reaction Scheme 1

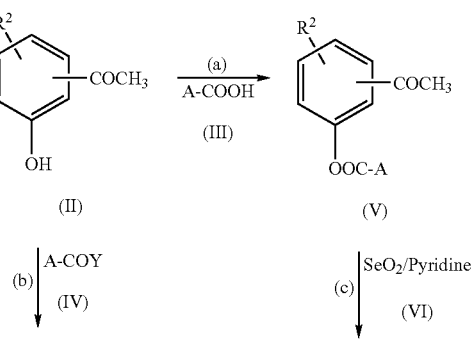

-continued

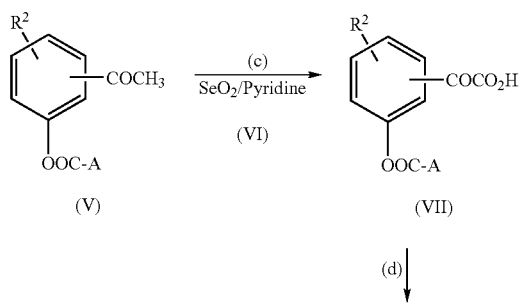

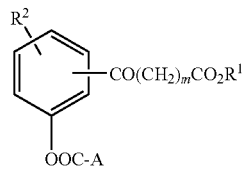

The compound of formula I where m is 1, $R^2$ is hydrogen, halo, alkoxy having from 1 to 3 carbon atoms or alkyl having from 1 to 3 carbon atoms, and $R^1$ is hydrogen or alkyl having from 1 to 3 carbon atoms, i.e. compounds of formula:

(I)

wherein A is described as above, can be prepared via reaction of Scheme 2. In the reaction scheme of Scheme 2, A, and $R^2$ are as above. $R^3$ is alkyl having from 1 to 3 carbon atoms.

The compound of formula V is synthesized in the same manner as described hereinbefore in connection with the reaction of steps (a) or (b) in Scheme 1. The compound of V is alkylated with the compound of formula VIII in the presence of base for example sodium hydride, sodium ethoxide and the like. Generally the reaction is carried out in solvents such as N,N-dimethylformamide, tetrahydrofuran and the like. Any of the conditions conventional for such alkylation reactions can be utilized to carry out the reaction of step (e).

The compound of formula IX is the compound of formula I where $R^1$ is alkyl having from 1 to 3 carbon atoms.

The compound of formula IX can be converted to the compound of formula I where $R^1$ is H by basic ester hydrolysis for example aqueous lithium hydroxide and the like via the reaction of step (f). Any conventional conditions for such ester hydrolysis can be utilized to produce the compound of formula I where $R^1$ is H.

If A is phenyl substituted by 1 or 2 groups of hydroxyl, it is generally preferred to protect the hydroxyl group with the suitable protecting group which protects the hydroxyl groups throughout the reaction. The suitable protecting group can be described in the Protective Groups in Organic Synthesis by T. Greene. The protecting group can be removed utilizing suitable deprotecting reagents such as those described in Protective Groups in Organic Synthesis by T. Greene. The products from each step can be isolated and purified by techniques such as extraction, evaporation, chromatography, and recrystallization.

Reaction Scheme 2

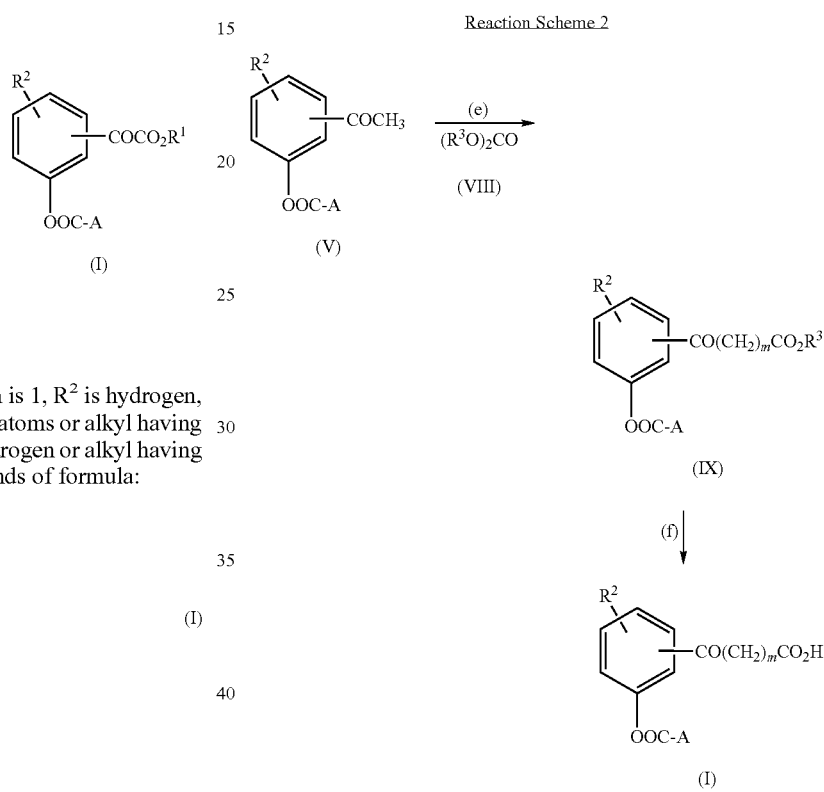

The compound of formula I where m is 2 to 8, $R^2$ is hydrogen, halo, alkoxy having from 1 to 3 carbon atoms or alkyl having from 1 to 3 carbon atoms, and $R^1$ is hydrogen or alkyl having from 1 to 3 carbon atoms, i.e. compounds of formula:

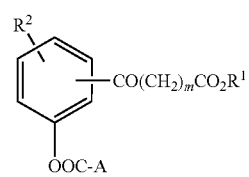

wherein A is described as above, can be prepared via reaction of Scheme 3.

In the reaction scheme of Scheme 3, A, $R^1$ and $R^2$ are as above. $R^4$ is a benzyl group and p is 1 to 7.

The compound of formula V is synthesized in the same manner as described hereinbefore in connection with the reaction of steps (a) or (b) in Scheme 1. The compound of formula V is converted to the compound of formula XI via reaction of step (g) by alkylating the compound of formula V tective Groups in Organic Synthesis by T. Greene after the reaction of step (i).

The products from each step can be isolated and purified by techniques such as extraction, evaporation, chromatography, and recrystallization.

Reaction Scheme 3

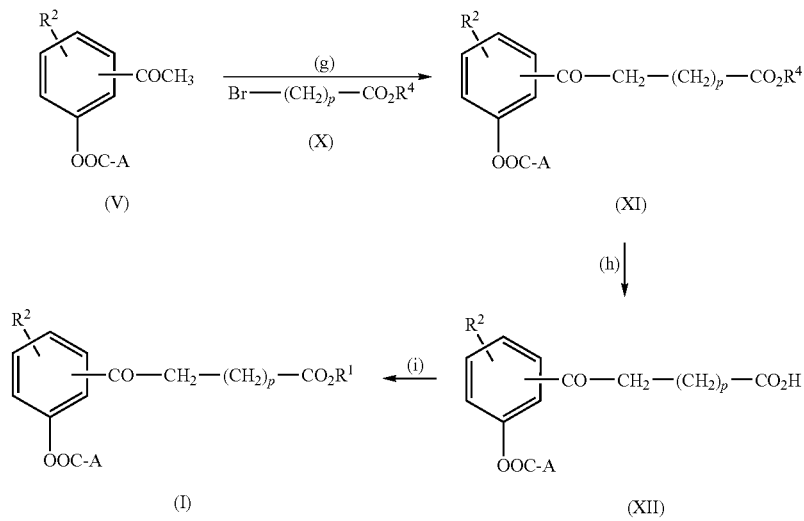

with the compound of formula X. This reaction is carried out in the presence of approximately a molar equivalent of a conventional base that converts acetophenone to 3-keto ester (i.e. gamma-keto ester). In carrying out this reaction it is generally preferred but not limited to utilize alkali metal salts of hexamethyldisilane such as lithium bis-(trimethylsilyl) amide and the like. Generally this reaction is carried out in inert solvents such as tetrahydrofuran: 1,3-Dimethyl-3,4,5,6-tetrahydro-2 (1H)-pyrimidinone. Generally the reaction is carried out at temperatures of from −65° C. to 25° C. Any of the conditions conventional in such alkylation reactions can be utilized to carry out the reaction of step (g).

The compound of formula XI is converted to compound of formula XII by hydrogenation via the reaction step of (h). The conventional method of hydrogenation consist of treating the compound of formula XI in an inert solvent for example ethyl acetate, ethanol and the like with hydrogen gas in the presence of a catalyst for example Pd—C. Any of the conditions conventional in such hydrogenation reactions can be utilized to carry out the reaction of step (h).

The compound of formula XII is the compound of formula I where $R^1$ is hydrogen.

The compound of formula XII can be converted to the compound of formula I via reaction of step (i) where $R^1$ is alkyl having 1 to 3 carbon atoms in the same manner as described hereinbefore in connection with the reaction of step (d) in Scheme 1.

If A is phenyl substituted by 1 or 2 groups of hydroxyl, it is generally preferred to protect the hydroxyl group with the suitable protecting group which protects the hydroxyl group throughout the reaction. The suitable protecting group can be described in the Protective Groups in Organic Synthesis by T. Greene. The protecting group can be removed after the alkylation in the case of compound of formula I where $R^1$ is H but for the compound of formula where $R^1$ is alkyl having from 1 to 3 carbon atoms, deprotection can be performed utilizing suitable deprotecting reagents such as those described in Pro- The compound of formula II where $R^2$ is hydrogen, halo, alkoxy having from 1 to 3 carbon atoms or alkyl having from 1 to 3 carbon atoms, i.e. compounds of formula:

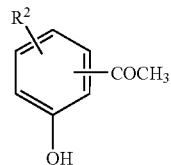

can be prepared via reaction of Scheme 4. In the reaction of Scheme 4, $R^2$ is as above. The compound of formula II can be synthesized according to the method of George M Rubottom et al., J. Org. Chem. 1983, 48, 1550-1552.

The product can be isolated and purified by techniques such as extraction, evaporation, chromatography, and recrystallization.

Reaction Scheme 4

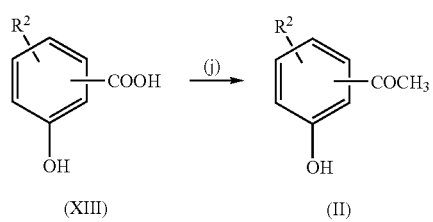

The compound of formula XIII where $R^2$ is halo, i.e. compounds of formula:

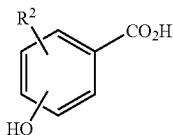

are either commercially available or can be prepared according to the methods described in the literature as follows:
1. 3-Br or F-2-OHC$_6$H$_3$CO$_2$H
Canadian Journal of Chemistry (2001), 79(11), 1541-1545.
2. 4-Br-2-OHC$_6$H$_3$CO$_2$H
WO 9916747 or JP 04154773.
3. 2-Br-6-OHC$_6$H$_3$CO$_2$H
JP 47039101.
4. 2-Br-3-OHC$_6$H$_3$CO$_2$H
WO 9628423.
5. 4-Br-3-OHC$_6$H$_3$CO$_2$H
WO 2001002388.
6. 3-Br-5-OHC$_6$H$_3$CO$_2$H
Journal of labelled Compounds and Radiopharmaceuticals (1992), 31(3), 175-82.
7. 2-Br-5-OHC$_6$H$_3$CO$_2$H and 3-Cl-4-OHC$_6$H$_3$CO$_2$H
WO 9405153 and U.S. Pat. No. 5,519,133.
8. 2-Br-4-OHC$_6$H$_3$CO$_2$H and 3-Br-4-OHC$_6$H$_3$CO$_2$H
WO 20022018323
9. 2-Cl-6-OHC$_6$H$_3$CO$_2$H
JP 06293700
10. 2-Cl-3-OHC$_6$H$_3$CO$_2$H
Proceedings of the Indiana Academy of Science (1983), Volume date 1982, 92, 145-51.
11. 3-Cl-5-OHC$_6$H$_3$CO$_2$H
WO 2002000633 and WO 2002044145.
12. 2-Cl-5-OHC$_6$H$_3$CO$_2$H
WO 9745400.
13. 5-I-2-OHC$_6$H$_3$CO$_2$H and 3-I, 2-OHC$_6$H$_3$CO$_2$H
Z. Chem. (1976), 16(8), 319-320.
14. 4-I-2-OHC$_6$H$_3$CO$_2$H
Journal of Chemical Research, Synopses (1994), (11), 405.
15. 6-I-2-OHC$_6$H$_3$CO$_2$H
U.S. Pat. No. 4,932,999.
16. 2-I-3-OHC$_6$H$_3$CO$_2$H and 4-I-3-OHC$_6$H$_3$CO$_2$H
WO 9912928.
17. 5-I-3-OHC$_6$H$_3$CO$_2$H
J. Med. Chem. (1973), 16(6), 684-7.
18. 2-I-4-OHC$_6$H$_3$CO$_2$H
Collection of Czechoslovak Chemical Communications, (1991), 56(2), 459-77.
19. 3-I-4-OHC$_6$H$_3$CO$_2$,
J.O.C. (1990), 55(18), 5287-91.

The compound of formula XIII, where $R^2$ is alkoxy having from 1 to 3 carbon atoms, and in which the substituents are arranged in the positions shown below:

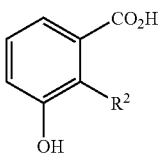

can be synthesized via the reaction of Scheme 5. In the reaction of Scheme 5, $R^2$ is as above, and $R^5$ is alkyl group having from 1 to 2 carbon atoms.

The compound of formula XIV can be converted to the compound of formula XV by reducing the aldehyde to primary alcohol. In carrying out this reaction, it is preferred but not limited to use sodium borohydride as the reducing reagent. Any of the conditions suitable in such reduction reactions can be utilized to carry out the reaction of step (k).

The compound of formula XV can be converted to the compound of formula XVI via reaction of step (l) by protecting 1-3 Diols by using 1,1,3,3-Tetraisopropyldisiloxane. The suitable conditions for this protecting group can be described in the Protective Groups in Organic Synthesis by T. Greene.

The compound of formula XVI can be converted to the compound of formula XVII via reaction of step (m) by protecting the phenol group by using benzyl bromide. The suitable conditions for this protecting group can be described in the Protective Groups in Organic Synthesis by T. Greene.

The compound of formula XVII can be converted to the compound of formula XVIII by deprotecting the silyl group using tetrabutylammonium fluoride via reaction of step (n). The suitable conditions for the deprotection can be described in the Protective Groups in Organic Synthesis by T. Greene.

The compound of formula XVIII can be converted to compound of formula XIX via reaction of step (o) by oxidation. Any conventional oxidizing group that converts primary alcohol to an acid for example chromium oxide and the like can be utilized to carry out the reaction of step (o).

The compound of formula XIX can be converted to the compound of formula XX by esterification of the compound of formula XIX with methanol or ethanol. The reaction can be carried out either by using catalysts for example H$_2$SO$_4$, TsOH and the like or by using dehydrating agents for example dicyclohexylcarbodiimide and the like. Any of the conditions conventional in such esterification reactions can be utilized to carry out the reaction of step (p).

The compound of formula XX can be converted to the compound of formula XXI by etherifying or alkylating the compound of formula XX with methyl halide or ethyl halide or propyl halide by using suitable base for example potassium carbonate, sodium hydride, triethylamine, pyridine and the like. The reaction is carried out in conventional solvents, for example tetrahydrofuran, N,N-dimethylformamide, dichloromethane and the like. The reaction is generally carried out at temperatures of from 0° C. to 40° C. Any of the conditions suitable in such alkylation reactions can be utilized to carry out the reaction of step (q).

The compound of formula XXI can be converted to the compound of formula XIII via reaction of step (r) by deprotection of ester and benzyl groups. The suitable deprotecting conditions can be described in the Protective Groups in Organic Synthesis by T. Greene.

The products from each step can be isolated and purified by techniques such as extraction, evaporation, chromatography, and recrystallization.

Reaction Scheme 5

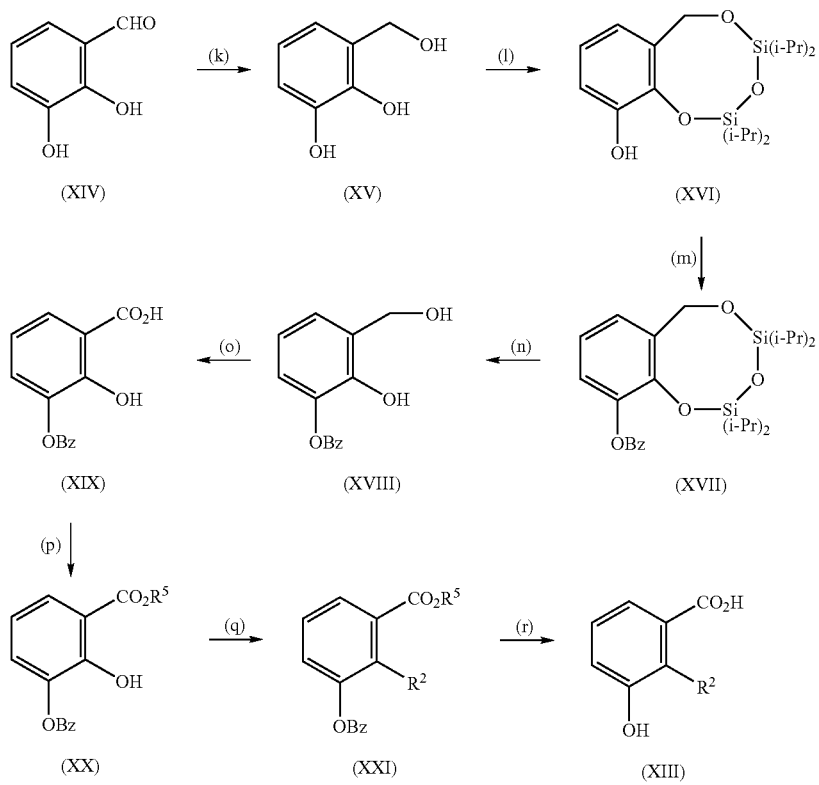

The compounds of formula XIII, where $R^2$ is alkoxy having from 1 to 3 carbon atoms, and in which the substituents are arranged in other positions, i.e. compounds of formula:

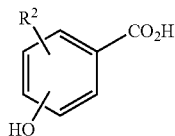

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO 9626176
6. 2-OEt-4-OHC$_6$H$_3$CO$_2$H
Takeda Kenkyusho Nempo (1965), 24, 221-8.
JP 07070025.
7. 3-OEt-4-OHC$_6$H$_3$CO$_2$H
WO 9626176.
8. 3-OPr-2-OHC$_6$H$_3$CO$_2$H
JP 07206658, DE 2749518.
9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4-OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24, 221-8 by using propyl halide.
13. 4-OEt-3-OHC$_6$H$_3$CO$_2$H
Biomedical Mass Spectrometry (1985), 12(4), 163-9.
14. 3-OPr-5-OHC$_6$H$_3$CO$_2$H
Adapt synthesis from Taiwan Kexue (1996), 49(1), 51-56 by using propyl halide.

The compound of formula XIII, where $R^2$ is alkyl having from 1 to 3 carbon atoms, i.e. compounds of formula:

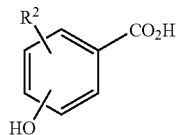

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.

3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem. (1981), 24(10), 1245-49.
13. 2-n-Pr-3-OHC$_6$H$_3$CO$_2$H
WO 9509843 and WO 9628423.
14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9
  by using ethyl alpha formylvalerate.
16. 3-n-Pr-4-OHC$_6$H$_3$CO$_2$H
Polymer (1991), 32(11) 2096-105.
17. 2-n-Pr-4-OHC$_6$H$_3$CO$_2$H
  3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
  Adapt synthesis from J.O.C. 2001, 66, 7883-88 by using 2-Ethylacrolein and 2-Propylacrolein.

The compound of formula X where p is 1 to 7 and R$^4$ is a benzyl group, i.e. compounds of formula:

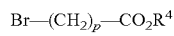

are either commercially available or can be prepared via the reaction scheme of Scheme 6.

Reaction Scheme 6

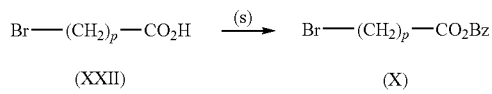

In the reaction of Scheme 6, p is as above.

The compound of formula XXII can be converted to the compound of formula X via reaction of step (s) by treating the compound of formula XXII with benzyl alcohol. The reaction can be carried out either by using catalysts for example H$_2$SO$_4$, TsOH or by using dehydrating reagents for example 1-(3-dimethylaminopropyl)-3-ethylcarbodiimide hydrochloride in the presence of catalytic amount of 4-di(methylamino)pyridine or dicyclohexylcarbodiimide and the like.

Any of the conditions conventional in such coupling reactions can be utilized to carry out the reaction of step (s).

The product can be isolated and purified by techniques such as extraction, evaporation, chromatography, and recrystallization.

Use in Methods of Treatment

This invention provides a method for treating a mammalian subject with a condition selected from the group consisting of insulin resistance syndrome, diabetes (both primary essential diabetes such as Type I Diabetes or Type II Diabetes and secondary nonessential diabetes) and polycystic ovary syndrome, comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. Compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitioneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type II diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

EXAMPLES

Example 1

Synthesis of Compound DP

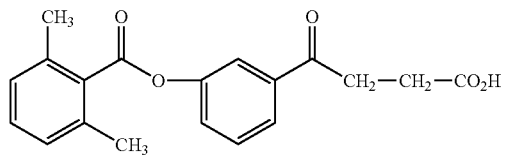 [SMILES: Cc1cccc(C)c1C(=O)Oc1cccc(C(=O)CCC(=O)O)c1]

4-(3-(2,6-Dimethylbenzoyloxy)phenyl)-4-oxobutanoic acid

Step A: Preparation of 2,6-Dimethylbenzoyl chloride 2,6-Dimethylbenzoic acid (15 g, 99.88 mmol) was added to anhydrous $CH_2Cl_2$ (20 ml) at 0° C. followed by drop wise addition of oxalyl chloride (2M in $CH_2Cl_2$, 14.14 g) under argon. The reaction mixture was stirred at the same temperature for 30 minutes and then warmed to the room temperature for 1 hour, concentrated and used without purification.

Step B: Preparation of 3-Acetylphenyl 2,6-dimethylbenzoate

To a stirred solution of 3'-Hydroxyacetophenone (4.84 g, 35.5 mmol) in anhydrous $CH_2Cl_2$ (50 ml) was added at room temperature pyridine (25 ml) followed by addition of 2,6-Dimethylbenzoyl chloride (Step A, 6 g, 35 mmol) in anhydrous $CH_2Cl_2$ (10 ml) under argon. The reaction mixture was stirred for 16 hours, concentrated under reduced pressure, diluted with $CH_2Cl_2$, and washed with 0.1M HCl, water and brine. The organic layer was dried over $Na_2SO_4$, concentrated and purified by flash chromatography eluted with ethyl acetate:hexane (1:2) to give the title compound.

$^1$H NMR (270 MHz, $CDCl_3$): 2.5 (s, 6H); 2.6 (s, 3H); 7.1 (m, 2H); 7.25 (m, 1H); 7.4-7.6 (m, 2H); 7.8-7.9 (m, 2H).

Step C: Preparation of 3-(4-(Benzyloxy)-4-oxobutanoyl)phenyl 2,6-dimethylbenzoate To a stirred solution of 3-Acetylphenyl 2,6-dimethylbenzoate (Step B, 2.90 g, 10.8 mmol) in dry THF (50 ml) and DMPU (17 ml) was added a solution of lithium bis(trimethylsilyl) amide (1.0M, 11.89 ml) at −65° C. under argon. After 10 minutes of stirring at −65° C., benzyl bromoacetate (3.72 g, 16.24 mmol) was added rapidly. The reaction mixture was stirred for an additional 10 minutes and then warmed to room temperature for 4 hours. The crude mixture was taken in ethyl acetate and washed with water and brine. The aqueous layer was extracted one more time with ethyl acetate. The combined organic layers were dried over $Na_2SO_4$, filtered, concentrated and purified by flash chromatography on a silica gel column (hex: ethyl acetate, 4:1) to provide the title compound.

$^1$H NMR (270 MHz, $CDCl_3$): 2.45 (s, 6H); 2.7 (t, 2H); 3.4 (t, 2H); 5.15 (s, 2H); 7.1 (m, 2H); 7.35-7.45 (m, 6H); 7.5-7.6 (m, 2H); 7.8-7.9 (m, 2H).

Step D: Preparation of 4-(3-(2,6-Dimethylbenzoyloxy)phenyl)-4-oxobutanoic acid

To a stirred solution of 3-(4-(Benzyloxy)-4-oxobutanoyl) phenyl 2,6-dimethylbenzoate (Step C, 2.75 g, 6.6 mmol) in ethyl acetate was added Pd—C (5%, 0.230 g) under an argon atmosphere. The starting material was hydrogenated under a $H_2$ atm for 14 hours and filtered through a celite pad. The filtrate was concentrated and purified by flash chromatography on a silica gel column (chloroform:methanol, 92.5:7.5 spiked with acetic acid) to provide the title compound.

$^1$H NMR (270 MHz, $CDCl_3$): 2.45 (s, 6H); 2.85 (t, 2H); 3.4 (t, 2H); 7.1 (m, 2H); 7.35 (m, 1H); 7.45-7.6 (m, 2H); 7.8-7.9.5 (m, 2H).

Example 2

Antidiabetic Effects of Compound DP in db/db Mice

Db/db mice have a defect in leptin signaling, leading to hyperphagia, obesity and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and randomly assigned into groups of 5-7 animals such that the body weights (40-45 g) and serum glucose levels ($\geqq 300$ mg/dl in fed state) were similar between groups; male lean (db/+heterozygote) mice served as cohort controls. A minimum of 7 days was allowed for adaptation after arrival. All animals were maintained under controlled temperature (23° C.), relative humidity (50±5%) and light (7:0-19:00), and allowed free access to standard chow (Formulab Diet 5008, Quality Lab Products, Elkridge, Md.) and water.

Mice received daily oral doses of vehicle or Compound DP (100 mg/kg/day) for 2 weeks. At the end of the treatment period 100 µl of venous blood was withdrawn in a heparinized capillary tube from the retro-orbital sinus for serum chemistry analysis.

After 2 weeks of daily oral dosing, Compound DP elicited a significant reduction in serum glucose and triglycerides (Table 1).

TABLE 1

Effects of Compound DP on serum glucose and triglycerides in db/db mice

|  | Glucose (mg/dL) | Triglycerides (mg/dL |
| --- | --- | --- |
| Lean | 212.6 ± 15.3 | 96.4 ± 6.4 |
| Vehicle | 752.9 ± 46.0 | 388.0 ± 50.7 |
| Compound DP | 264.3 ± 96.8* | 140.8 ± 20.6* |

*$p < 0.05$ significantly different compared with vehicle-control

What is claimed is:

1. A compound of the formula:

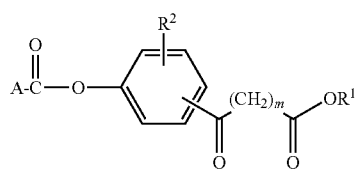

I wherein
m is 0, 1, 2, 3, 4, 5, 6, 7 or 8;
$R^1$ is hydrogen or alkyl having from 1 to 3 carbon atoms;
$R^2$ is hydrogen, halo, alkyl having from 1 to 3 carbon atoms, or alkoxy having from 1 to 3 carbon atoms;
A is phenyl, independently substituted at each of the 2-position and the 6-position by a substituent selected from the group consisting of: chloro, bromo, iodo, hydroxy, alkyl having 1 or 2 carbon atoms, perfluoromethyl; alkoxy having 1 or 2 carbon atoms, and perfluoromethoxy;
or a pharmaceutically acceptable salt of the compound.

2. The compound or salt of claim 1, wherein m is 2 or 4; $R^2$ is hydrogen; and
A is phenyl, independently substituted at each of the 2-position and the 6-position by a substituent selected from the group consisting of: chloro, bromo, iodo, hydroxy, alkyl having 1 or 2 carbon atoms, and perfluoromethyl.

3. The compound or salt of claim 2, wherein A is 2,6-dimethylphenyl.

4. The compound or salt of claim 1 wherein the compound is 4-(3-(2,6-Dimethylbenzoyloxy)phenyl)-4-oxobutanoic acid.

5. A pharmaceutical composition adapted for oral administration, comprising a pharmaceutically acceptable carrier and from one milligram to four hundred milligrams of a biologically active agent, wherein the agent is a compound of the formula:

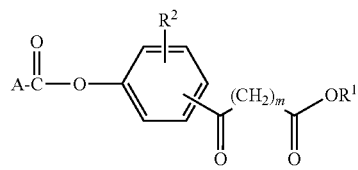

I wherein
m is 0, 1, 2, 3, 4, 5, 6, 7 or 8;
$R^1$ is hydrogen or alkyl having from 1 to 3 carbon atoms;
$R^2$ is hydrogen, halo, alkyl having from 1 to 3 carbon atoms, or alkoxy having from 1 to 3 carbon atoms;
A is phenyl, independently substituted at each of the 2-position and the 6-position by a substituent selected from the group consisting of: chloro, bromo, iodo, hydroxy, alkyl having 1 or 2 carbon atoms, perfluoromethyl; alkoxy having 1 or 2 carbon atoms, and perfluoromethoxy;
or a pharmaceutically acceptable salt of the compound.

6. The pharmaceutical composition of claim 5, wherein m is 2 or 4; $R^2$ is hydrogen; and
A is phenyl, independently substituted at each of the 2-position and the 6-position by a substituent selected from the group consisting of: chloro, bromo, iodo, hydroxy, alkyl having 1 or 2 carbon atoms, and perfluoromethyl.

7. The pharmaceutical composition of claim 6, wherein A is 2,6-dimethylphenyl.

8. The pharmaceutical composition of claim 7 wherein the compound is 4-(3-(2,6-Dimethylbenzoyloxy)phenyl)-4-oxobutanoic acid.

9. The pharmaceutical composition of claim 5 in oral unit dosage form.

10. The pharmaceutical composition of claim 5 for use in the treatment of a condition selected from the group consisting of insulin resistance syndrome, diabetes, polycystic ovary syndrome, hyperlipidemia, fatty liver disease, cachexia, obesity, atherosclerosis, arteriosclerosis.

11. The compound or salt of claim 1, wherein A is phenyl, independently substituted at each of the 2-position and the 6-position by a substituent selected from the group consisting of: chloro, bromo, iodo, hydroxy, alkyl having 1 or 2 carbon atoms, and perfluoromethyl.

12. The pharmaceutical composition of claim 5, wherein A is phenyl, independently substituted at each of the 2-position and the 6-position by a substituent selected from the group consisting of: chloro, bromo, iodo, hydroxy, alkyl having 1 or 2 carbon atoms, and perfluoromethyl.

* * * * *